US009989470B1

(12) United States Patent
Pangarkar et al.

(10) Patent No.: US 9,989,470 B1
(45) Date of Patent: Jun. 5, 2018

(54) METHODS AND DEVICES FOR SAMPLE ANALYSIS

(71) Applicant: Theranos IP Company, LLC, Newark, CA (US)

(72) Inventors: Chinmay Pangarkar, Palo Alto, CA (US); Karan Mohan, Palo Alto, CA (US)

(73) Assignee: Theranos IP Company, LLC, Newark, CA (US)

( * ) Notice: Subject to any disclaimer, the term of this patent is extended or adjusted under 35 U.S.C. 154(b) by 0 days. days.

(21) Appl. No.: 15/161,650

(22) Filed: May 23, 2016

Related U.S. Application Data

(63) Continuation of application No. 14/309,888, filed on Jun. 19, 2014, now Pat. No. 9,562,860.

(60) Provisional application No. 61/837,167, filed on Jun. 19, 2013.

(51) Int. Cl.
*G01N 15/02* (2006.01)
*G01N 21/64* (2006.01)
*G01N 15/14* (2006.01)

(52) U.S. Cl.
CPC ..... *G01N 21/6486* (2013.01); *G01N 15/1434* (2013.01); *G01N 15/1459* (2013.01)

(58) Field of Classification Search
CPC ........... G01N 21/6486; G01N 21/6458; G01N 21/255; G01N 21/33; G01N 2201/062; G01N 15/1434; G01N 15/1459; G01N 30/74; G01N 1/28; G01N 35/00; A61B 1/00096; G06K 9/00; H04N 1/04; G02B 21/36; H01S 3/10
See application file for complete search history.

(56) References Cited

U.S. PATENT DOCUMENTS

| | | | |
|---|---|---|---|
| 3,854,044 A | 12/1974 | Stay et al. | |
| 5,270,212 A * | 12/1993 | Horiuchi | G01N 1/28 356/244 |
| 5,414,508 A | 5/1995 | Takahashi et al. | |
| 6,088,097 A | 7/2000 | Uhl | |
| 6,396,580 B1 | 5/2002 | Tewes | |
| 6,599,475 B1 | 7/2003 | Berndt et al. | |
| 6,603,537 B1 | 8/2003 | Dietz et al. | |
| 8,313,713 B2 | 11/2012 | Jacobs et al. | |
| 2001/0028497 A1 | 10/2001 | Uhl | |

(Continued)

FOREIGN PATENT DOCUMENTS

| | | |
|---|---|---|
| CN | 201156031 | 11/2008 |
| EP | 0781987 A2 | 7/1997 |

(Continued)

OTHER PUBLICATIONS

Notice of Allowance dated Sep. 23, 2016 for U.S. Appl. No. 14/309,888.

(Continued)

*Primary Examiner* — Jamil Ahmed

(57) ABSTRACT

Methods and devices for cytometric analysis are provided. A cytometry apparatus is provided which may be used with a stationary sample cuvette for analysis of a stationary sample or with a flow sample cuvette for analysis of a flowing sample. The methods and devices provided herein may be used to perform cytometric analysis of samples under a wide range of experimental and environmental conditions.

20 Claims, 4 Drawing Sheets

(56) References Cited

U.S. PATENT DOCUMENTS

| | | | |
|---|---|---|---|
| 2002/0122246 A1* | 9/2002 | Tearney | A61B 1/00096 |
| | | | 359/368 |
| 2003/0104494 A1 | 6/2003 | Ravkin et al. | |
| 2003/0202905 A1 | 10/2003 | Devlin et al. | |
| 2003/0205681 A1 | 11/2003 | Modlin | |
| 2003/0236458 A1 | 12/2003 | Hochman | |
| 2004/0126005 A1 | 7/2004 | Duvdevani et al. | |
| 2005/0153435 A1 | 7/2005 | Archibald | |
| 2005/0237605 A1 | 10/2005 | Vodyanoy et al. | |
| 2006/0043301 A1 | 3/2006 | Mantele et al. | |
| 2006/0166305 A1 | 7/2006 | Jiang et al. | |
| 2006/0215400 A1 | 9/2006 | Lewis et al. | |
| 2007/0035818 A1 | 2/2007 | Bahatt et al. | |
| 2007/0242277 A1 | 10/2007 | Dolfi et al. | |
| 2009/0190822 A1 | 7/2009 | Ortyn et al. | |
| 2009/0196482 A1* | 8/2009 | Kobayashi | G01N 21/6458 |
| | | | 382/133 |
| 2009/0274176 A1* | 11/2009 | O'Shaughnessy | G01N 21/255 |
| | | | 372/9 |
| 2010/0014158 A1 | 1/2010 | Nihoshi | |
| 2010/0128256 A1 | 5/2010 | Thomson | |
| 2011/0064628 A1 | 3/2011 | Thomas et al. | |
| 2011/0242535 A1 | 10/2011 | Frose | |
| 2012/0002029 A1 | 1/2012 | Sieracki et al. | |
| 2013/0050782 A1* | 2/2013 | Heng | G01N 15/1434 |
| | | | 358/494 |
| 2013/0088221 A1 | 4/2013 | Van et al. | |
| 2014/0030737 A1 | 1/2014 | Holmes et al. | |
| 2014/0038206 A1 | 2/2014 | Holmes et al. | |
| 2014/0193892 A1 | 7/2014 | Mohan et al. | |
| 2014/0273188 A1 | 9/2014 | Mohan et al. | |
| 2015/0031051 A1 | 1/2015 | Mohan et al. | |
| 2015/0153272 A1* | 6/2015 | Ehring | G01N 30/74 |
| | | | 250/373 |

FOREIGN PATENT DOCUMENTS

| | | |
|---|---|---|
| JP | 2006162427 A | 6/2006 |
| JP | 2007127449 A | 5/2007 |
| JP | 2010091679 A | 4/2010 |
| JP | 2010091809 A | 4/2010 |
| JP | 2011118264 A | 6/2011 |
| TW | 201224425 A | 6/2012 |
| WO | 2002093141 A1 | 11/2002 |
| WO | 2009142312 A1 | 11/2009 |
| WO | 2012178069 A | 12/2012 |
| WO | 2014018805 A2 | 1/2014 |
| WO | 2014127372 A2 | 8/2014 |

OTHER PUBLICATIONS

Office Action dated Sep. 9, 2016 for U.S. Appl. No. 14/508,137.
Advisory Action dated Feb. 8, 2016 for U.S. Appl. No. 13/951,449.
Advisory Action dated Apr. 14, 2016 for U.S. Appl. No. 14/309,888.
Advisory Action dated Apr. 28, 2016 for U.S. Appl. No. 13/951,063.
Dhawan et al. Multispectral Optical Imaging of Skin-Lesions for Detection of Malignant Melanomas. Proceeding of the 31st Annual International Conference of the IEEE Engineering in Medicine and Biology Society: Engineering the Future of Biomedicine, EMBC 2009, IEEE, Sep. 3, 2009, pp. 5352-5355.
International Search Report and Written Opinion dated Sep. 11, 2014 for Application No. PCT/US2014/016962.
Lee et al. Integrated optical molecular imaging system for four-dimensional real-time detection in living single cells, Biosensors and Bioelectronics, Elsevier BV, NL, vol. 31 No. 1, Oct. 27, 2011, pp. 393-398.
Notice of Allowance dated Mar. 25, 2016 for U.S. Appl. No. 13/951,449.
Notice of Allowance dated Apr. 14, 2016 for U.S. App. No. 14/161,639.
Office Action dated Jan. 15, 2016 for U.S. Appl. No. 14/508,137.
Office Action dated Jan. 4, 2016 for U.S. Appl. No. 14/161,639.
Office Action dated Feb. 1, 2016 for U.S. Appl. No. 14/309,888.
Office Action dated Feb. 24, 2016 for U.S. Appl. No. 13/951,063.
Office Action dated May 12, 2016 for U.S. Appl. No. 14/508,137.
Office Action dated May 6, 2015 for U.S. Appl. No. 13/951,449.
Office Action dated Jun. 12, 2015 for U.S. Appl. No. 14/161,639.
Office Action dated Jun. 5, 2015 for U.S. Appl. No. 14/508,137.
Office Action dated Jul. 8, 2015 for U.S. Appl. No. 13/951,063.
Office Action dated Aug. 21, 2015 for U.S. Appl. No. 14/309,888.
The International Search Report and the Written Opinion dated Mar. 24, 2014 for Application No. PCT/US2013/052141.
Thompson, Fluorescence Correlation Spectroscopy, Topics in Fluorescence Spectroscopy, Jan. 1, 2002, Kluwer Academic Publishers, Boston.
U.S. Appl. No. 14/600,630, filed Jan. 20, 2015.
Office Action dated Oct. 6, 2017 for U.S. Appl. No. 14/630,544.

* cited by examiner

METHODS AND DEVICES FOR SAMPLE ANALYSIS

CROSS-REFERENCE TO RELATED APPLICATIONS

This applications claims the benefit of, and priority to U.S. Provisional Patent Application No. 61/837,167, filed Jun. 19, 2013, the content of which is hereby incorporated by reference in its entirety for all purposes.

BACKGROUND

Cytometric analysis of a sample can provide a wealth of information about the sample, such as the number and type of cells or other particles in the sample, specific molecules which may be present in the sample, and other information.

While a large number of systems and devices for the analysis of samples are known, there is a need for improved systems for cytometric analysis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Provided herein are devices and methods for sample analysis.

In an embodiment, a cytometry apparatus is provided. The cytometry apparatus may be configured to receive cytometry cuvettes which are configured for analysis of stationary or flowing samples. The cytometry apparatus may be used to obtain information from stationary or flowing samples.

In embodiments, the cytometry apparatus may direct light from a sample to a first optical pathway or a second optical pathway, where the first optical pathway contains one or more image sensors and the second optical pathway contains one or more light detectors.

In embodiments, devices and methods provide herein may be used and performed in micro-gravity environments.

In embodiments, provided herein is a cytometry apparatus comprising: a stage, wherein the stage is configured to receive and support a cytometry cuvette, wherein the cytometry cuvette is configured to receive and support a biological sample, and wherein the cytometry cuvette comprises a sample plane on which the biological sample is supported; an objective, wherein the objective comprises an entrance pupil and an exit pupil, and wherein the objective is optically coupled to the stage such that light from the biological sample supported by the cytometry cuvette supported by the stage may enter the entrance pupil and exit the exit pupil; a first detection train, wherein the first detection train comprises one or more image sensors; a second detection train, wherein the second optical pathway comprises one or more light detectors; an actuatable structure for directing light, wherein the actuatable structure is configured to direct light from the exit aperture of the objective to the first detection train or the second detection train; and an illumination train, wherein the illumination train comprises a light source, wherein the illumination train is configured to provide at least a first illumination output and a second illumination output, and wherein for the first illumination output the illumination train is configured to focus light of a first range of wavelengths from the light source on a first location on the sample plane of the cytometry cuvette and the illumination train is configured to focus light of a second range of wavelengths from the light source on a second location on the sample plane of the cytometry cuvette. Other related cytometry apparatuses, systems and methods are also provided.

In embodiments, in systems and methods provided herein, a sample may be loaded into a cytometry cuvette before the cuvette is moved to a stage of a cytometry apparatus, or after the cuvette is moved to the stage of the cytometry apparatus.

In embodiments, a stage of a cytometry apparatus provided herein may have an opening. In embodiments, the opening may have no material in the opening. In other embodiments, the opening may have an optically transmissive material (e.g. glass, clear plastic, etc.).

In embodiments, a sample provided herein may contain multiple cells. Multiple cells typically includes at least two cells. In embodiments, context indicate that a sample described herein as containing "multiple cells" may contain more than two cells, such as at least 4, 5, 6, 7, 9, 10, or more cells.

In embodiments a focal point in a flow cytometry cuvette has a diameter of at least 10, 20, 30, 40, 50, 60, 70, 80, 90, 100, 150, or 200 microns, a diameter of no more than 10, 20, 30, 40, 50, 60, 70, 80, 90, 100, 150, 200, or 300 microns, or a diameter of at least 10, 20, 30, 40, 50, 60, 70, 80, 90, 100, 150, or 200 microns and no more than 20, 30, 40, 50, 60, 70, 80, 90, 100, 150, 200, or 300 microns. In embodiments the space between focal points in a flow channel may be least 10, 20, 30, 40, 50, 60, 70, 80, 90, 100, 150, or 200 microns, no more than 10, 20, 30, 40, 50, 60, 70, 80, 90, 100, 150, 200, or 300 microns, or at least 10, 20, 30, 40, 50, 60, 70, 80, 90, 100, 150, or 200 microns and no more than 20, 30, 40, 50, 60, 70, 80, 90, 100, 150, 200, or 300 microns.

In embodiments, a light source provided herein may provide continuous light, or it may intermittently provide light. For example, it may provide flashes of light to coincide with the timing of the movement of cells through a flow channel of a flow sample cuvette.

In embodiments, references herein to "cells" in systems and methods provided herein also apply to similarly sized and shaped small objects (e.g. particles, beads, etc.), unless the context dictates otherwise.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

Figure 1:
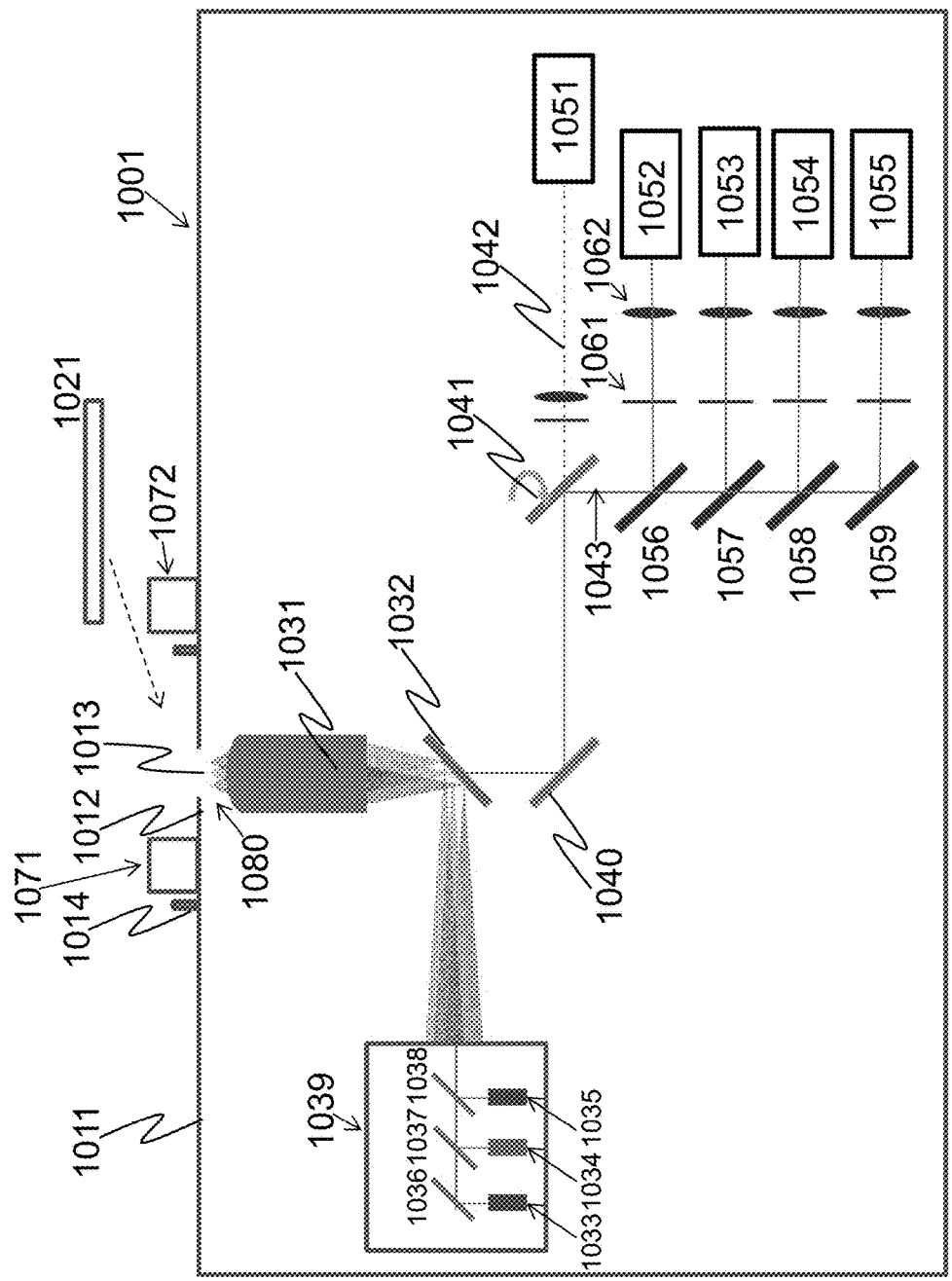
FIG. 1 shows an exemplary schematic of a cytometry apparatus.

It is noted that the drawings and elements therein are not necessarily drawn to shape or scale. For example, the shape or scale of elements of the drawings may be simplified or modified for ease or clarity of presentation. It should further be understood that the drawings and elements therein are for exemplary illustrative purposes only, and not be construed as limiting in any way.

DETAILED DESCRIPTION

While various embodiments of the invention are shown and described herein, these are provided by way of example only. It should be understood that there is no intent to limit the invention to the particular forms disclosed, but rather, the invention is to cover all modifications, equivalents, and alternatives falling within the spirit and scope of the invention provided herein.

As used herein, references to a "sample" refer to the sample as a whole or any portion thereof, unless the context clearly dictates otherwise. For example, a description of an image of a "sample" may refer to an image of a single cell within the sample, or it may refer to an image of a field of view of a sample within a cuvette, which may contain, for example, one or more cells, no cells, one or more non-cellular particles, or any combination thereof.

As used herein, descriptions of objects being in "optical communication" refer to objects which are spatially positioned such that they may be directly or indirectly optically coupled. An object which is in optical communication with another object may, for example, emit light, reflect light, transmit light, or absorb light. Objects which are in optical communication may be positioned from each other in a straight path (e.g. a light source and a light sensor may be in a straight line relative to each other, such that light travels in a straight line between the light source and light sensor), or they may be at an angle to each other, with one or more structures positioned between the objects which to change the direction of movement of light (e.g. a light source and a light sensor may be at a 90 degree angle relative to each other, with an angled mirror being situated in the light path between the light source and light sensor, such that light from the light source is reflected off the mirror at a 90 degree angle towards the light sensor). Also, light does not need to be continuously moving between two objects for them to be considered to be in optical communication. For example, a light source and light sensor are considered to be in optical communication if the light source and light sensor are situated such that light from the light source can reach the light sensor under selected conditions; light from the light source does not need to continuously reach the light sensor for them to be considered to be in optical communication. In another example, an object which may reflect light (e.g. a cytometry cuvette) may be considered to be in optical communication with a light source which emits light which strikes the object or with a light sensor which absorbs light reflected by the object. As used herein, objects described as being in "optical communication" may also be described as being "optically coupled".

In embodiments, provided herein is a cytometry apparatus. The cytometry apparatus may be configured to obtain at least a 2-dimensional or 3-dimensional image of a sample. The cytometry apparatus may be configured to obtain multiple images of a sample over a period of time. The cytometry apparatus may alternatively or additionally be configured to detect light of one or more selected wavelength(s) emitted by or scattered by a sample. A cytometry apparatus may be used to obtain information relating to, for example, cells, crystals, particles, or other small objects.

The cytometry apparatus may contain a stage. The stage may be configured to receive a cytometry cuvette, slide, or other structure which may contain a sample for cytometric analysis. The stage may contain an opening through which light may pass between a cuvette and an objective (discussed further below) adjacent to or in optical communication with the cuvette.

The cytometry apparatus may contain one or more light sources. The light source may be, for example, a tungsten bulb, a tungsten-halogen bulb, an arc lamp (e.g. mercury, xenon, zirconium, or metal halide), a laser (e.g. argon-ion laser, krypton-ion laser), or a light-emitting diode. A light source may emit light which has approximately uniform brightness across the wavelengths of the visible spectrum (e.g. white light), or it may emit light of variable brightness across the visible spectrum (e.g. a lamp, such as a mercury arc lamp, may emit light having brightness peaks at 365, 405, 436, 546, and 579 nm). In embodiments, a light source may emit light having a single peak of brightness in the visible spectrum. For example, LEDs may emit light of only a single brightness peak, which may have a spectral width (i.e. the width of the emission peak at 50% maximum intensity/full width at half maximum (FWHM)) of, for example, 1, 2, 3, 4, 5, 10, 15, 20, 25, 30, 35, 40, 50, 60, 70, 80, 90, 100, or 200 nm. Different LEDs may have brightness peaks at different wavelengths. For example, an LED may have brightness peak at, for example, 365, 400, 445, 455, 465, 470, 505, 525, 530, 535, 565, 585, 590, 595, 625, or 635 nm.

In embodiments, the cytometry apparatus may contain 1, 2, 3, 4, 5, 6, 7, 8, 9, 10, 11, 12, 13, 14, 15, 20, 25, 30, 35, 50, 100, 500, 1000, or more light sources. In a cytometry apparatus containing two or more light sources, the light sources may be all of the same type (e.g. all lasers or all LEDs), or the light sources may be of two or more different types (e.g. a tungsten bulb and a mercury arc lamp). In a cytometry apparatus containing two or more light sources, the light sources may have the same or different emission brightness peak(s).

The cytometry apparatus may contain an objective. The objective may contain one or more lenses and may serve to capture light from a sample in a cuvette on the stage. The objective may also be positioned in the apparatus such that light from the light source(s) is directed into and through the objective to a cuvette on the stage. In embodiments, the objective may also function as a condenser such that the light is focused onto the sample in the cuvette as it passes through the objective. The position of the objective, the stage, the cuvette, or other component of the cytometry apparatus may be adjusted in order to focus the light from the objective onto the sample or to collect light from the sample.

In embodiments, a light source may be in-line with the objective, such that light travels in a straight path from the light source to the objective. In other embodiments, a light source may be at an angle to the objective, such light is directed in a non-straight path from the light source to the objective. For example, a light source may be situated at a 90 degree angle from the aperture of the objective, and the light from the light source may be directed to the aperture of the objective by, for example, a mirror or fiber optics. In embodiments, a mirror which directs light from a light source into the objective may be a dichroic mirror. A dichroic mirror may reflect light above or below a given cutoff wavelength, and may transmit light on the opposite side of the cutoff wavelength. For example, a particular dichroic mirror may have a cutoff wavelength of 425 nm, and it may transmit 90% of light at 440-700 nm and reflect 90% of light at 380-410 nm. In another example, another dichroic mirror may also have a cutoff wavelength of 425 nm, but it may reflect 90% of light at 440-700 nm and transmit 90% of light at 380-410 nm. Dichroic mirrors are available, for example, from Thorlabs, Inc. (Newton N.J.). As used herein, "dichroic mirrors" also may include mirrors that are polychroic—i.e. which transmit or reflect multiple ranges of wavelengths of light.

The objective may also be configured to capture light emitted from or scattered by the sample. For example, light of a first wavelength may be directed through the objective onto a sample in a cuvette on the stage. The sample may contain a fluorescent molecule which is excited by light of the first wavelength. Upon excitation by light of the first wavelength, the fluorescent molecule may emit light of a second wavelength. The emitted light from the fluorescent molecule may travel back through the objective and into the interior of the cytometry apparatus.

In embodiments, light passing from the sample through the objective may encounter a dichroic mirror downstream from the objective (i.e. after passing through the objective). The dichroic mirror may be the same mirror which reflected light from the light source into the aperture of the objective. Light of one or more wavelengths from the objective may be transmitted through the dichroic mirror. As discussed above, different dichroic mirrors may transmit or reflect different wavelengths or ranges of wavelengths of light.

The cytometry apparatus may contain one or more sensors for detecting light emitted, reflected, or scattered from a sample in a cuvette. Sensors for detecting light (also referred to herein as "optical sensors") may include image sensors and light detectors.

In embodiments, the cytometry apparatus may contain an image sensor capable of obtaining at least a two-dimensional image of an object. As used herein, an "image sensor" refers to a device which can convert an optical image into one or more electrical signals. Image sensors include, for example, charge-coupled device (CCD), complementary metal-oxide semiconductor (CMOS), and hybrid CCD/CMOS (e.g. sCMOS) sensors. Digital cameras contain an image sensor such as a CCD or CMOS sensor, and, in embodiments, a digital camera itself may be referred to as an image sensor. Generally, a single image sensor contains an array of a large number of photoactive structures (e.g. capacitors, photodiodes), such that when the image sensor is exposed to light, each of the many photoactive structures generates an electric charge proportional to the light intensity on the respective structure, thereby initiating the conversion of an image into an electrical signal. In embodiments, the photoactive structures of an image sensor may be referred to as "pixels", and an image sensor may be referred to as a "pixelated" sensor. In embodiments, an image sensor may be used to generate a three-dimensional image of an object, by, for example, using a processor to combine multiple optical images obtained with an image sensor. In embodiments, an image sensor may be used to generate an image of an object over time, by collecting multiple images of the object with the image sensor. An image sensor may be used to record video of a sample.

In embodiments, the cytometry apparatus may contain a light detector. As used herein, a "light detector" refers to a non-pixelated/non-arrayed light sensor. An individual "light detector" as used herein is capable of detecting photons of light, but not of converting an optical image into an electrical signal. Examples of "light detectors" as used herein include, for example, photomultiplier tubes (PMT), photodiodes, and avalanche photodiodes. In embodiments, a light detector may have greater light sensitivity than an image sensor. In embodiments, a light detector may be optically coupled to one or more optical filters such that only light a selected range of wavelengths is permitted to reach the light detector.

In embodiments, light which has been emitted or scattered from a sample and passed through the objective of a cytometry apparatus provided herein may be directed into an optical pathway in which the light may be selectively directed into a first optical pathway towards one or more imaging sensors or into a second optical pathway towards one or more light detectors. Light may be selectively directed into a first or second optical pathway by use of one or more structure for the direction of light such as, for example, a mirror, fiber optics, prism, lens, filter, or a combination thereof. In embodiments, a structure for directing the path of light may be coupled to an actuation mechanism (e.g. an electric motor, a pneumatic actuator, hydraulic piston, relay, comb drive, piezoelectric actuator, thermal bimorph, digital micromirror, or an electroactive polymer). The actuation mechanism may be coupled to a controller. The controller may be configured to receive protocols or instructions from, for example, a user, local memory, or an external database. The controller may provide instructions to the actuation mechanism to change the position of the hardware for directing the path of light, in order to control the direction of the light.

In embodiments, an optical pathway in which light may be selectively directed towards an imaging sensor or light detector may contain one or more mirrors to direct light towards a selected optical sensor. A mirror in an optical pathway may be used in various different ways to direct light towards a selected pathway or sensor. For example, in embodiments, a mirror may be movable by an actuation mechanism such that in a first position it is in the path of light coming from the objective of the cytometry apparatus (and it therefore reflects the light from the objective), and in a second position it is not in the path of light coming from the objective of the cytometry apparatus (and it therefore does not reflect or otherwise interfere with the light from the objective). By such a mechanism, a mirror may selectively directing light from the objective to a first or a second optical pathway. In another example, in embodiments, a mirror may be movable by an actuation mechanism such that in a first position it reflects the light from the objective at a first angle, and in a second position it reflects light the from the objective at a second angle, thereby selectively directing light from the objective to a first or a second optical pathway.

In embodiments, an optical pathway containing one or more light detectors may contain 1, 2, 3, 4, 5, 6, 7, 8, 9, 10, 15, 20, 25, 50, or more light detectors. A plurality of light detectors in an apparatus may be arranged such that different detectors of the plurality are each positioned to receive light of different ranges of wavelengths. For example, an optical pathway containing three light detectors may contain a first light detector configured to receive light of 400-500 nm, a second light detector configured to receive light of 500-600 nm, and a third light detector configured to receive light of 600-700 nm.

Various materials may be used in an optical pathway containing one or more light detectors in order to restrict the wavelength(s) of light that reach a given light detector. For example, a light detector may be behind a filter or monochromator, which may transmit light of only a limited range of wavelengths (blocking the transmission of light of wavelengths outside of the limited transmission range). In another example, a dichroic mirror may be provided in an optical pathway containing one or more light detectors. The dichroic mirror may be positioned such that, for example, it reflects light of certain wavelengths to a light detector or such that it transmits light of certain wavelengths to a light detector. In embodiments, an optical pathway containing a dichroic mirror may contain two or more light detectors, such that light reflected by the dichroic mirror is detected, and also such that light transmitted by the dichroic mirror is detected.

As used herein, an "optical pathway" may also be referred to as an "optical train". Also, an optical train containing materials and a configuration specialized for emitting light may be referred to herein as an "illumination train", and an optical train containing materials and a configuration specialized for detecting light may be referred to as a "detection train". An optical train may include, for example, one or more of and any combination of lenses, mirrors, prisms, grating elements, light sources, light sensors, or other materials for guiding the movement of, emitting, or detecting light. An illumination train typically comprises at least a light source, and a detection train typically comprises at least an optical sensor.

In embodiments, a cytometry apparatus may contain one or more image sensors and one or more light detectors. In embodiments, the objective of the cytometry apparatus may be configured to be in optical communication with both image sensor(s) and light detector(s), such that light emitted or reflected from a sample through the objective may be detected by one or more image sensor or light detector. In some embodiments, the cytometry apparatus may be configured such that light from the objective is directed to either the image sensor(s) or light detector(s). In other embodiments, the cytometry apparatus may be configured such that some light from the objective is directed to the image sensor(s) (e.g. light of a first range of wavelengths) and other light from the objective is directed to the light detector(s) (e.g. light of a second range of wavelengths). The cytometry apparatus may contain one or more mechanisms to direct light from the sample to the image sensor(s) and/or the light detector(s), as discussed above.

The cytometry apparatus may also contain light sources and optical sensors which are not in optical communication with the objective of the apparatus. For example, the cytometry apparatus may contain one or more light sources or optical sensors which are in the same or similar plane as a sample in a cuvette on the stage. The plane may be parallel to, or at a different angle (e.g. 15, 30, 45, 60, 75, or 90 degrees) relative to the cuvette. This type of light source or detector may be referred to herein as a "sample coplanar" or "non-objective-linked" light source or optical sensor, and may have any of the features of light sources or optical sensors described elsewhere herein. In some embodiments, a sample coplanar/non-objective-linked light source or optical sensor may have any orientation in which it is in optical communication with a sample in a cuvette. In embodiments, a cuvette for use with a cytometry apparatus may contain one or more openings or optical pathways to permit light from a sample coplanar light source to reach the sample in the cuvette or to permit light scattered or emitted from the sample to travel to a sample coplanar optical sensor. In an embodiment, a sample coplanar light source generates white light and a corresponding sample coplanar optical sensor detects light across the visible spectrum. In embodiments, 1, 2, 3, 4, 5, 6, 7, 8, 9, 10, or more sample coplanar light sources or optical sensors may be provided in relation to a cytometry apparatus stage. In some embodiments, fiber optics may be used to connect an optical pathway to or from a cuvette to a sample coplanar optical sensor or light source. Through the use of fiber optics, two or more optical pathways in a cuvette may be operably connected to a single sample coplanar optical sensor or light source. For example, a first end of a fiber optic cable may be permanently attached to an optical sensor or light source. However, the second of the cable may be moveable such that it may be attached to different optical pathways in the cuvette. This may permit multiple optical configurations to be generated with the same cuvette. In some embodiments, a sample coplanar optical sensor is a light detector, as described herein.

In embodiments, sample coplanar light sources or optical sensors may be provided which are within a housing of the cytometry apparatus. In other embodiments, sample coplanar light sources or optical sensors may be provided which are not within a housing of the cytometry apparatus. In still other embodiments, sample coplanar light sources or optical sensors may be provided which are not part of the cytometry apparatus, but which are in electrical or optical communication with the apparatus.

A schematic of an example cytometry apparatus is provided in FIG. 1. FIG. 1 shows a side view of the exemplary cytometry apparatus. The exemplary cytometry apparatus 1001 may have a housing 1011 and a stage 1012. The stage 1012 may be configured to receive and support a cuvette 1021. The stage 1012 may contain an opening 1013 through which light may travel from an objective 1031 to a sample in a cuvette 1021 and from a sample in a cuvette 1021 to an objective 1031 in the cytometry apparatus. The stage 1012 may also contain one or more supports 1014 to aid in the positioning of a cuvette on the stage. A dichroic mirror 1032 may be present and situated so as to reflect to the objective 1031 light of certain wavelengths from one or more light sources 1033, 1034, 1035 and to transmit light from the sample (and the objective) of certain wavelengths. In the exemplary apparatus of FIG. 1, three light sources 1033, 1034, and 1035 are present. The light sources 1033, 1034, 1035 are LEDs, each with a different range of emission wavelengths. The light sources 1033, 1034, 1035 may be arranged in a larger compound light source 1039 which contains one or more of the light sources 1033, 1034, 1035 and which may direct light from the one or more light sources, such as through the use of dichroic mirrors 1036, 1037, 1038. Light from the light source 1039 may have any configuration; for example, although FIG. 1 depicts the light as being focused, with a focal point at the dichroic mirror 1032, the light from the light source may be collimated and not focused on the mirror 1032. Also, in embodiments, collimated light may be reflected from the mirror into the objective. In certain configurations, light from the objective may focus light of one or more selected ranges of wavelengths onto one or more locations. For example, in FIG. 1, light of a first selected range of wavelengths from the light source is focused on a first location, light of a second selected range of wavelengths from the light source is focused on a second location, and light of a third selected range of wavelengths from the light source is focused on a third location (collectively indicated by 1080). A mirror 1040 may be included which is configured to reflect light transmitted through the dichroic mirror 1032. Also, although not depicted in FIG. 1, in embodiments, one or more actuatable lens may be present, which may be moved between the light source 1039 and the mirror 1040. Positioning of the actuatable lens between the light source 1039 and the mirror 1040 may configure light for use with obtaining images of stationary samples with an image sensor. The cytometry apparatus may contain an actuatable mirror 1041, which can be moved to selectively direct light from the objective to either a first optical pathway 1042 towards one or more imaging sensors or to a second optical pathway 1043 towards one or more light detectors. In the exemplary apparatus of FIG. 1, the actuatable mirror 1041 may be moved to at least a first position or a second position. In the first position (not shown), the actuatable mirror 1041 is positioned such that it does not interfere with the movement of light from the mirror 1040 (i.e. it is positioned out of the way of the path of light), and, as a result, the light travels along the first optical pathway 1042 which leads to an image sensor 1051. In the second position (shown), the actuatable mirror 1041 is position such that it reflects light from the 1040 (i.e. it is position in the way of the path of the light), and, as a result, the light is directed to the second optical pathway 1043, which leads to a collection of light detectors 1052, 1053, 1054, and 1055. Accordingly, light from the objective may be selectively directed towards the first optical pathway 1042 or the second optical pathway 1043. Dichroic mirrors 1056, 1057, 1058, 1059 may be included in the second optical pathway 1043. The dichroic mirrors 1056, 1057, 1058, 1059 in the second optical pathway may separate the light in the second optical pathway into multiple different light paths, based on the light wavelength. The light of different wavelength ranges may, in turn, be directed to different light detectors 1052, 1053, 1054, 1055. In embodiments, the first optical pathway 1042, second optical pathway 1043, or portions thereof may further include one or more filters 1061 or lenses 1062 (for clarity, only a single filter and lens is notated in the figure). The filter 1061 may transmit only a limited range of wavelength(s), and the lens 1062 may focus the light onto the image sensor or light detector.

The exemplary cytometry apparatus of FIG. 1 may further contain a sample coplanar light source 1071 and a sample coplanar optical sensor 1072.

The stage of the cytometry apparatus may be configured to receive and support a variety of different structures which may contain a sample for cytometric analysis. Structures which may contain a sample may be referred to, for example, as cytometry cuvettes or slides. Typically, a stage will support a cytometry cuvette by the cuvette resting on top of the stage. In other embodiments, a stage may be configured support a cytometry cuvette from above the cuvette, such as by containing a slot for the cuvette, or by having structures to attach a cuvette (e.g. magnets, screws, clamps, etc.). A cytometry cuvette or slide which contains a sample may also be described as "supporting" a sample. Samples may be loaded into cytometry cuvettes, and cuvettes may be described as "receiving" a sample. Cytometry cuvettes or slides may have different configurations.

In some embodiments, a cytometry cuvette may be configured to retain a sample in a stationary position. These cuvettes may be referred to herein as "stationary sample cuvettes". In such cuvettes, components of a sample (e.g. cells, crystals, etc.) may, for example, settle to the floor of the sample well of the cuvette, and may be sensed (e.g. imaged) while stationary on the floor of the sample well. In embodiments, two or three-dimensional images of stationary sample may be obtained with an image sensor. Such images, for example, may be of cells or other components of a sample. These images may provide a wealth of information about a selected component(s) of a sample. For example, in the case of a cell, an image may provide, for example, information regarding cell size, cell morphology, cell staining pattern, etc. Images of a sample obtained with an image sensor may be analyzed with automated programs.

Figure 2:
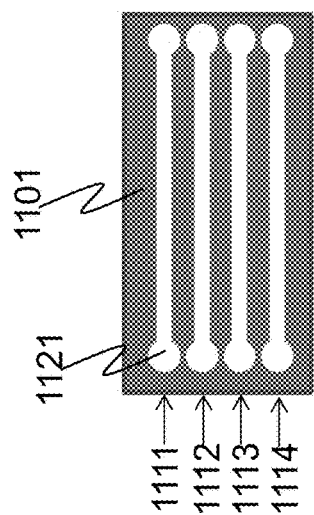
FIG. 2 shows an exemplary schematic of a stationary sample cuvette.

A schematic of an example cuvette for stationary sample analysis is provided in FIG. 2. FIG. 2 shows a top-down view the exemplary cuvette for stationary sample analysis. The exemplary cuvette 1101 contains four sample wells 1111, 1112, 1113, and 1114. A cuvette for stationary sample analysis may contain any number of sample wells, such as 1, 2, 3, 4, 5, 6, 7, 8, 9, 10, 11, 12, 13, 14, 15, 20, 25, 30, 40, 50, 60, 70, 80, 90, 100, 200, 300, 400, 500, or more wells. A sample well may have any shape that permits it to support a sample. For example, a sample well may be circular, elongated, square, etc. The sample wells may be fluidically isolated. Fluidically isolated wells may be advantageous, for example, to permit the loading of multiple different samples onto the same cuvette. Different samples may be, for example, samples from the same subject that has been treated differently (e.g. stained with different markers, dyes, etc.), or samples from different subjects. A sample well may have one or more ports 1121 for loading sample into the cuvette (each of the wells in FIG. 2 contains two ports; however, for clarity, only a single port is annotated in the Figure).

In some embodiments, a cytometry cuvette may be configured to support the flow of a sample from a first location to a second location within the cuvette. These cuvettes may be referred to herein as "flow sample cuvettes". In flow sample cuvettes, a sample may, for example, move from a first location in the cuvette (e.g. the location where the sample is introduced into the cuvette) to a second location in the cuvette (e.g. a sample collection area). As a sample moves from a first location to a second location in the cuvette, components of the sample (e.g. cells) may also move locations. In embodiments, a flow sample cuvette may contain a port for introduction of sample into the cuvette, a sample collection area, and a channel connecting the sample introduction port and the sample collection area. The channel may be enclosed. The channel may have dimensions which are only a small amount larger than the diameter of cells of interest for analysis in the cuvette. For example, the channel may have a height, width, both height and width, or diameter of no greater than 10, 15, 20, 25, 30, 35, 40, 45, 50, 60, 70, 80, 90, or 100 microns. The channel of the cuvette may have any orientation relative to the cuvette or the cytometry apparatus. For example, relative to a horizontal stage, the channel may be also be horizontal or it may be vertical or at an angle. Fluid may be propelled through the channel by a variety of different forces, such as, for example, capillary action, gravity, positive pressure from a force behind the liquid, or negative pressure in front of the liquid. In embodiments, positive pressure may be exerted on a liquid in a channel by a pipette tip which loads sample into the channel through the sample introduction port and provides sufficient force on the sample to propel the sample through the channel. In embodiments, a sample collection area may have an air vent, to relieve pressure generated by the movement liquid towards or into the sample collection area.

In embodiments, light from a light source may by directed at the channel of a flow sample cuvette. In embodiments, light from the objective may be focused on or close to one or more particular location in the channels of a flow sample cuvette (a "focal point" in the channel). At a focal point, light of a selected range of wavelengths from the light source may be focused. At a focal point in the channel, light from the objective may be at a relatively high intensity, such that a greater amount of light may strike a cell at the focal point in the channel than would strike a cell in a stationary sample cuvette on the same cytometry apparatus. Accordingly, in some embodiments, when using the same cytometry apparatus, individual cells may be excited with greater light intensity when they are in a flow sample cuvette than in a stationary sample cuvette. In some situations, it may be desirable to contact a sample with a relatively high light intensity in order, for example, to increase the intensity of scattered or emitted light from the sample. Increasing the intensity of light from a sample may, in turn, for example, increase the speed or sensitivity at which a sample or component therein may be detected.

In embodiments, an illumination train of a cytometry apparatus provided herein may be configured to focus light of 1, 2, 3, 4, 5, 6, 7, 8, 9, 10, 15, 20 or more ranges of wavelengths at one or more different locations in a flow channel of a flow cytometry cuvette. For example, in order to interrogate a sample and cells therein flowing through the flow channel of a flow cytometry cuvette for fluorescence, it may be desirable to focus light of a first range of wavelengths at a first location in the channel, in order to excite a first type of fluorescent marker which may be on cells which has a first peak (maximum) excitation wavelength and it may be desirable to focus light of a second range of wavelengths at a second location in the channel, in order to separately excite a separate type of fluorescent marker which may be on cells which has a second peak excitation wavelength. As is discussed further below, in embodiments, by spatially separating the locations at which a cell may be exposed to focused light of different ranges of wavelengths, information from a cell may be efficiently obtained. A range of wavelengths that may be focused may be, for example, a range of 200, 100, 90, 80, 70, 60, 50, 40, 30, 25, 20, 15, 10, 5, or fewer nanometers. In embodiments, the range may be centered around the peak excitation wavelength of a particular fluorescent marker of interest. For example, the fluorphore fluorescein has a peak excitation wavelength of 494 nanometers; a range of 20 nanometers around the 494 nanometer peak may be selected as the range of wavelengths, such that light of 484-504 nanometers is focused at a location in the channel of a flow sample cuvette. In another example, a range of 30 nanometers around the 494 nanometer peak may be selected as the range of wavelengths, such that light of 479-509 nanometers is focused. Other ranges of wavelengths may be selected based on other fluorescent markers, as appropriate. In embodiments, a range of wavelengths may be, for example, selected based on the color of the focused light, such as between 620-645 nanometers (red light), 520-550 nanometers (green light), 490-520 nanometers (cyan light), or 460-490 (blue light).

In some embodiments, light emitted or scattered by a sample in a flow sample cuvette may be detected by a light detector of the cytometry apparatus, after the light has travelled through the objective of the cytometry apparatus and been directed to a detection train optical pathway downstream of the objective which leads to one or more light detectors. For example, light detectors downstream of the objective may be configured to detect emitted light from the sample of one or more selected wavelengths. In embodiments, light detectors downstream of the objective may be configured for detection of fluorescent light emission from samples. Thus, in some embodiments, light detectors downstream of the objective may be used for detecting fluorescent molecules in a sample in a flow sample cuvette. Typically, for fluorescence analysis of samples in a flow sample cuvette, light of one or more selected wavelengths is directed to the sample from the objective in the cytometry apparatus. The light source for this light may be located in the cytometry apparatus, and it may be filtered to contain only a selected range of wavelengths.

In embodiments, light emitted or scattered by a sample in a flow sample cuvette may be detected by a light detector of the cytometry apparatus. This light may provide, for example, information regarding the presence of a marker on a cell, nucleic acid content of a cell, cell shape, etc. In embodiments, any information that can be obtained from a traditional flow cytometer may be obtained with a cytometry apparatus and flow sample cuvette as provided herein.

In some embodiments, light emitted or scattered by a sample in a flow sample cuvette may be detected by a sample coplanar optical sensor. A flow sample cuvette may contain one or more openings or optical pathways to permit light scattered or emitted from the sample in the channel of the flow sample cuvette to travel to a sample coplanar optical sensor. A flow sample cuvette may additionally or alternatively contain one or more openings or optical pathways to permit light from a sample coplanar light source to reach the sample. In embodiments, an optical pathway from the channel of the flow sample cuvette to a coplanar optical sensor may be at, for example, a 5, 10, 15, 20, 25, 30, 35, 40, 45, 50, 65, 70, 75, 80, 85, 90, 95, 100, 105, 110, 115, 120, 125, 130, 135, 140, 145, 150, or 180 degree angle relative to an optical pathway to the channel from a coplanar light source. In some embodiments, a flow sample cuvette may have 1, 2, 3, 4, 5, 6, 7, 8, 9, 10 or more openings or optical pathways to permit light from a sample to travel to a sample coplanar optical sensor. In a flow sample cuvette having two or more optical pathways to a sample coplanar optical sensor, the optical pathways to the sensors may be at different angles relative to an optical pathway from a coplanar light source (e.g. if the flow sample cuvettes contains two optical pathways to a sample coplanar optical sensor, the first optical pathway may be at a 15 degree angle relative to the optical pathway from the coplanar light source, and the second optical pathway may be at a 45 degree angle relative to the optical pathway from the coplanar light source). In some embodiments, as discussed above, through the use of fiber optics, different optical pathways in flow sample cuvette may be connected to the same optical sensor or light source. In some embodiments, it may be advantageous to measure light scattering of a sample with one or more sample coplanar optical sensors, rather than with one or more optical sensors which are downstream of the objective. For example, if a flow sample cuvette contains a narrow optical pathway from the channel to an optical sensor, scattered light of a very limited range may be collected. Scatter information of a sample from a narrow optical pathway may provide more information for sample analysis that may be provided from a wider scatter range. While the objective in a cytometry apparatus may collect scattered light, typically, it may do so from a relatively large area, and thus, it may contain less information.

Figure 3A:
FIGS. 3A and 3B show an exemplary schematic of a flow sample cuvette; 3A shows a side view and 3B shows a top-down view.
Figure 3B:
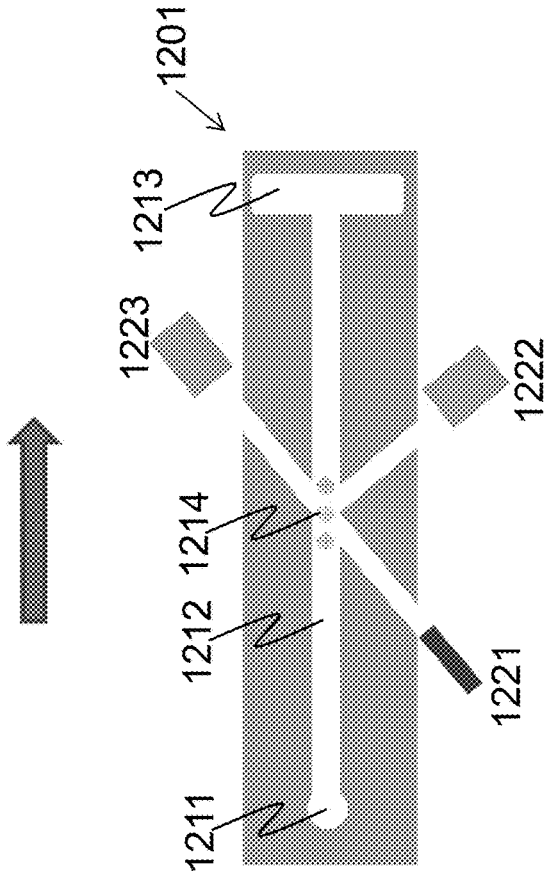

A schematic of an example cuvette for flow sample analysis is provided in FIG. 3. FIG. 3A shows a top-down view and FIG. 3B shows a side-view of the exemplary cuvette for flow sample analysis. The exemplary cuvette 1201 contains a sample introduction port 1211, flow channel 1212, and sample collection area 1213. Light from the objective may have one or more focal point 1214 in the channel 1212. For example, in FIG. 3B, light of three selected ranges of wavelengths is focused onto three separate locations in the flow channel (collectively indicated by the three dots 1214). As indicated in FIG. 3 by the direction of the arrow, sample flows from left to right in the example cuvette. FIG. 3B further shows exemplary positions of a sample coplanar light source 1221 and optical sensors 1222, 1223. The optical pathway of the first optical sensor 1222 is at a 90 degree angle to the optical pathway of the light source 1221, while the optical pathway of the second optical sensor 1223 is in-line (at an 180 degree angle) to the optical pathway of the light source 1221. Optical pathways to the sample coplanar light source and optical sensors may intersect with at least one focal point 1214 in the channel 1212.

Figure 4:
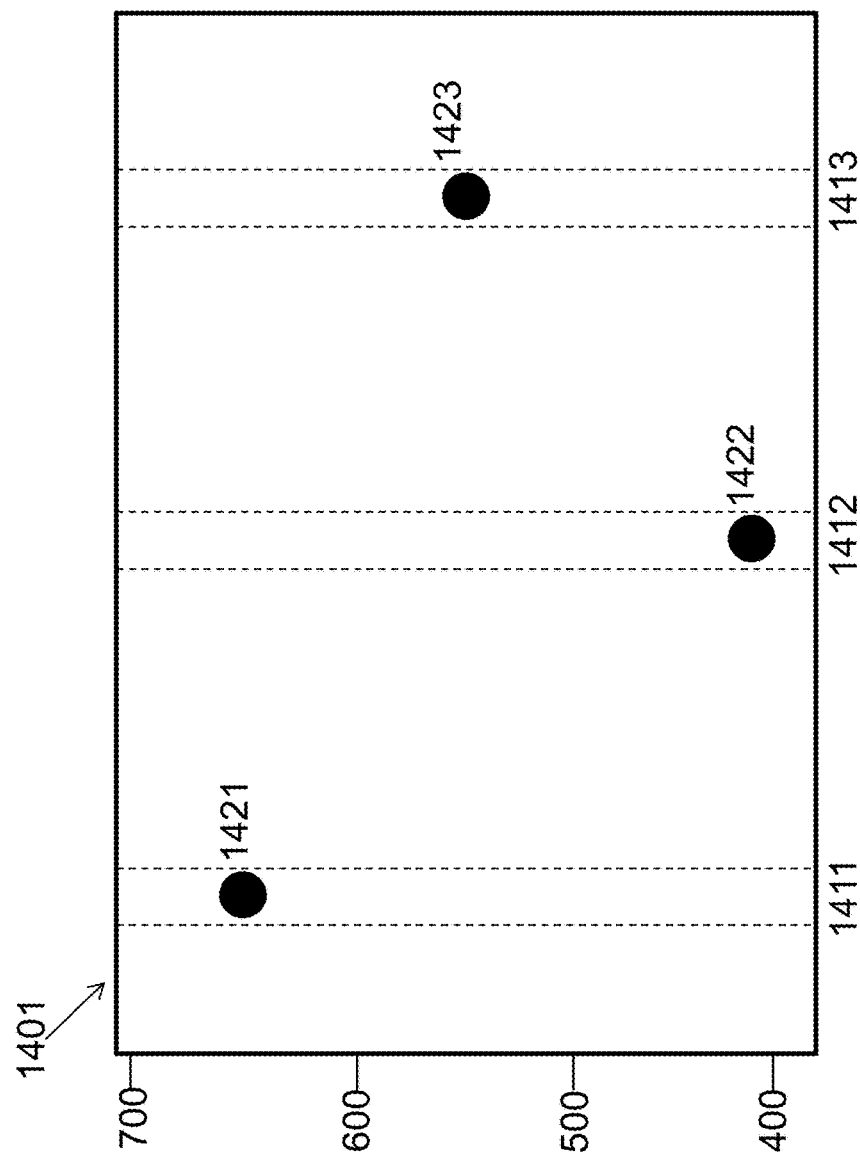
FIG. 4 shows an exemplary schematic of an image that can be obtained by an image sensor of a cytometry apparatus.

In embodiments, when an illumination train of a cytometry apparatus provided herein focuses light of two or more ranges of wavelengths at two or more different locations in a flow channel of a flow cytometry cuvette, light emitted from objects present at the respective locations may be separately detected. For example, a cytometry apparatus provided herein may focus light of a first range of wavelengths on a first location in a flow channel of a flow cytometry cuvette, and may focus light of a second range of wavelengths on a second location in a flow channel of a flow cytometry cuvette. As a sample containing cells is flowed through the flow channel, cells may pass through the first location in the flow channel and then the second location in the flow channel. The cells may be labeled with different fluorescent markers, which have different excitation peaks. The excitation peak of the first fluorescent marker on the cells may overlap with the focused light of the first range of wavelengths, and the excitation peak of the second fluorescent marker on the cells may overlap with the focused light of the second range of wavelengths. In such a circumstance, a cell labeled with the first fluorescent marker will emit light at the first fluorescent marker's emission spectrum when it is illuminated by the focused light of the first range of wavelengths. Similarly, a cell labeled with the second fluorescent marker will emit light at the second fluorescent marker's emission spectrum when it is illuminated by the focused light of the second range of wavelengths. The light emitted by the cell may be detected by one or more optical sensor. For example, in an embodiment, a cytometry apparatus and flow sample cuvette may be configured such that during the flow of a sample containing cells through the flow channel of a flow sample cuvette, a single cell at a time passes through a region in the flow channel containing each of the different locations in the flow channel where light of a range of wavelengths. Such a region may be referred to as a "detection region" herein. For example, the flow channel of a flow sample cuvette on a stage of a cytometry apparatus may have light of the wavelengths 390-420 focused on a first location in the flow channel, it may have light of the wavelengths 460-490 focused on a second location in the flow channel, and it may have light of the wavelengths 530-560 focused on a third location in the flow channel. These three locations and the space between them may be collectively referred to as the "detection region" of the flow channel of the flow sample cuvette. Thus, in embodiments, a cytometry apparatus and flow sample cuvette may be configured such that during the flow of a sample containing cells through the flow channel of a flow sample cuvette, a single cell at a time passes through the detection region. As the cell passes through the detection region, if the cell contains a fluorescent marker which is excited by a wavelength of light focused on a respective location, the fluorescent marker on the cell will emit light which may be detected the cytometry apparatus. For example, the cell may be labeled with a first fluorescent marker which has a peak excitation wavelength of 400 nm and with a second fluorescent marker which has a peak excitation wavelength of 545 nm. This cell will thus fluoresce when it passes through the first location and the third location (but not the second location) in the flow channel of the example provided above. The emitted light from the cell can be detected by a detection train as provided herein. For example, light from the different locations in the detection region may be captured by the objective and directed to a detection train containing one or more light detectors. In other embodiments, a cytometry apparatus and flow sample cuvette may be configured such that during the flow of a sample containing cells through the flow channel of a flow sample cuvette, one cell per location of focused light of a range of wavelengths in the detection region flows through the detection region. For example, in the configuration described above (which has 3 locations in the flow channel with a focused light of a range of wavelengths), the sample and system may be configured so that 3 cells flow through the detection region at a time. In such embodiments, at certain instances during the flow, one cell may be present at each of the different locations having focused light of a range of wavelengths. Such a set up may permit a more rapid analysis of cells than a configuration in which only a single cell at a time is flowed through the detection region. In embodiments in which multiple cells flow through a detection region at the same time, light emitted from cells may be detected through various detection train configurations. In embodiments, the emitted light from multiple cells in the detection region may be detected by light detectors in a detection train comprising appropriate filters, lenses, mirrors, or other hardware for separating and detecting the relevant emitted light. In other embodiments, the emitted light from multiple cells in the detection region may be detected by an image sensor in a detection train comprising appropriate filters, lenses, mirrors, or other hardware for separating and detecting the relevant emitted light. For example, an objective may simultaneously capture light from cells in multiple different locations having focused light of a range of wavelengths in a flow channel. The light may be directed to an detection train which includes a prism or diffraction grating for separating light based on the wavelength of the light. Such a detection train may permit a single image obtained by an image sensor to contain information regarding cells at multiple different positions in a flow channel, each position being a location having focused light of a range of wavelengths, and also in which the cells may emit light of different wavelengths. For example, FIG. 4 provides an exemplary schematic of an image that may be obtained by an image sensor in a detection train as described immediately above. In the example for FIG. 4, an image is taken when one cell is at each of three different locations in the flow channel having focused light of a range of wavelengths. The focused range of wavelengths for the different locations may be the same or different. The light emitted from the cell present at each location is captured by the objective, and passed through a prism, diffraction grating, or other structure to separate light based on wavelength. In FIG. 4, the image 1401 contains information from each of the three locations in the flow channel having focused light of a range of wavelengths. In the image 1401, along the X-axis positions 1411, 1412, and 1413 correspond to the three locations in the flow channel having focused light of a range of wavelengths. Along the Y-axis, the numbers 400, 500, 600, and 700 indicate wavelengths of light. The parallel dotted lines for each of 1411, 1412, and 1413 are not in the actual image, but indicate a virtual line along which the emitted light for each respective position may be located. The black dots 1421, 1422, and 1423 indicate the wavelength of light which is sensed by the image sensor for each of the 1411, 1412, and 1413 positions. Thus, in the exemplary image of FIG. 4, the cell present at the first location in the flow channel emitted light having a peak intensity of approximately 650 nm, the cell present in the second location in the flow channel emitted light having a peak intensity of approximately 410 nm, and the cell present in the third location in the flow channel emitted light having a peak intensity of approximately 550 nm.

In embodiments in which the illumination train focuses light of two or more ranges of wavelengths at two or more different locations in a flow channel of a flow cytometry cuvette, the the illumination train may remain in the same configuration regardless of whether the emitted light from interrogated cells is to be detected by a light detector or an image sensor.

As an example of an analysis that may be performed with systems and method provided herein, a blood sample may be obtained from a subject. White blood cells may be isolated from the blood sample. The white blood cells may be treated with three different antibodies, each antibody being directed to a different cell surface marker optionally present on the surface of white blood cells (e.g. CD45, CD14, and CD3), each antibody being labeled with a different fluorescent marker, and each different fluorescent marker having a different peak excitation wavelength. The sample may be flowed through a flow sample cuvette as provided herein. As the sample flows through flow channel of the cuvette, cells (or other particles in the sample) may pass through three locations in the flow channel which are exposed to focused light of a range of wavelengths. As the cells pass through each of the first location, the second location, and the third location, the focused light may excite the fluorescent marker present on an antibody used to label the cell. If the fluorescent marker is excited, it may emit light at its emission wavelength, and this light may be detected as described elsewhere herein. The detected light may be analyzed to determine information regarding the cells flowed through the cuvette.

The cytometry apparatus may have a housing. The housing may contain one or more of the components of the cytometry apparatus within the housing. In some embodiments, all of the components of the cytometry apparatus are within the housing. In some embodiments, the stage is on the surface of the housing, and cytometry cuvettes are supported outside the housing. In some embodiments, cytometry cuvettes loaded onto a stage inside the housing.

In embodiments, methods and devices as provided herein may be used in micro-gravity environments. For example, a flow sample cuvette as provided herein may be used to perform sample assays in micro-gravity conditions. As described above, a flow sample cuvette contains a narrow channel through which the sample moves and is exposed to light. This channel may be of a dimension such that cells or particles may only travel through the channel in single-file. Accordingly, a sample in a flow sample cuvette may be positioned in the cuvette in the same way whether under standard gravity or micro-gravity environments.

Biological samples may be analyzed with systems and methods provided herein. The biological sample may be a bodily fluid, a secretion, or a tissue sample. Examples of biological samples may include but are not limited to, blood, serum, saliva, urine, gastric and digestive fluid, tears, stool, semen, vaginal fluid, interstitial fluids derived from tumorous tissue, ocular fluids, sweat, mucus, earwax, oil, glandular secretions, breath, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk or other excretions. The sample may be provided from a human or animal. Samples may be from a plant, microorganism (e.g. virus, bacteria), or other biological material. Biological samples may contain cells, crystals, particles, or other small objects. Cells in a biological sample may be separate from each other, or they may be linked together. In embodiments, linked cells may be treated in order to separate them into individual, free-moving cells. Cells may be prokaryotic or eukaryotic. In embodiments, a biological sample may be a blood sample, or a portion thereof. In embodiments, cells in a biological sample may be white blood cells. In embodiments, a blood sample containing red blood cells and white blood cells may be treated with a reagent to lyse the red blood cells and stabilize white blood cells. Such stabilized white blood cells may be analyzed with a system or method provided herein.

In embodiments, cells may be prepared for cytometry by systems and methods provided herein by any method known in the art. Cells may be optionally fixed, stained, or otherwise labeled with a detectable marker. Cells may be fixed with a variety of methods known in the art, including but not limited to heat, freeze, perfusion, immersion, and chemical fixation. Chemical fixation may be achieved by a wide variety of agents, including but not limited to crosslinking agents (such as formaldehyde, glutaraldehyde, other aldehydes, and their derivatives), precipitating agents (such as ethanol and other alcohols), oxidizing agents (such as osmium tetroxide or potassium permanganate), potassium dichromate, chromic acid, mercury-containing fixatives, acetic acid, acetone, picrates, and HOPE fixative. Cells may also be permeabilized, such as through the use of surfactants, as may be useful for subsequent internal labeling or staining.

Cells may be stained with any optically detectable dye, stains, or coloring agents, such as nucleic acid dyes (including intercalator dyes), lipophilic dyes, protein dyes, carbohydrate dyes, heavy metal stains. Such dyes and stains or staining processes include but are not limited to Acid Fast Bacilli staining, Alcian Blue staining, Alcian Blue/PAS staining, Alizarin Red, alkaline phosphatase staining, aminostyryl dyes, ammonium molybdate, Azure A, Azure B, Bielschowsky Staining, Bismark brown, cadmium iodide, carbocyanines, carbohydrazide, carboindocyanines, Carmine, Coomassie blue, Congo Red, crystal violet, DAPI, ethidium bromide, Diff-Quik staining, eosin, ferric chloride, fluorescent dyes, fuchsin, Giemsa stain, Golgi staining, Golgi-Cox staining, Gomori's Trichrome staining, Gordon Sweet's staining, Gram staining, Grocott Methenamine staining, haematoxylin, hexarnine, Hoechst stains, Hyaluronidase Alcian Blue, indium trichloride, indocarbocyanines, indodicarbocyanines, iodine, Jenner's stain, lanthanum nitrate, lead acetate, lead citrate, lead(II) nitrate, Leishman stain, Luna staining, Luxol Fast Blue, Malachite green, Masson Fontana staining, Masson Trichrome staining, methenamine, methyl green, methyline blue, microglia staining, Miller's Elastic staining, neutral red, Nile blue, Nile red, Nissl staining, Orange G, osmium tetroxide, Papanicolaou staining, PAS staining, PAS diastase staining, periodic acid, Perls Prussian Blue, phosphomolybdic acid, phosphotungstic acid, potassium ferricyanide, potassium ferrocyanide, Pouchet staining, propidium iodide (PI), Prussian Blue, Renal Alcian Blue/PAS staining, Renal Masson Trichrome staining, Renal PAS Methenamine staining, Rhodamine, Romanovsky stain, Ruthenium Red, Safranin O, silver nitrate, Silver staining, Sirius Red, sodium chloroaurate, Southgate's Mucicannine, Sudan staining, Sybr Green, Sybr Gold, SYTO dyes, SYPRO stains, thallium nitrate, thiosemicarbazide, Toluidine Blue, uranyl acetate, uranyl nitrate, van Gieson staining, vanadyl sulfate, von Kossa staining, WG staining, Wright-Giemsa stain, Wright's stain, X-Gal, and Ziehl Neelsen staining. Cells may be treated with uncolored dye precursors that are converted to a detectable product after treatment, such as by enzymatic modification (such as by peroxidases or luciferases) or binding to an ion (such as Fe ions, $Ca^{2+}$ or $H^+$).

In embodiments, cells may be labeled with fluorescent markers. Useful fluorescent markers include natural and artificial fluorescent molecules, including fluorescent proteins, fluorophores, quantum dots, and others. Some examples of fluorescent markers that may be used include but are not limited to: 1,5 IAEDANS; 1,8-ANS; 5-carboxy-2,7-dichlorofluorescein; 5-Carboxyfluorescein (5-FAM); fluorescein amidite (FAM); 5-Carboxynapthofluorescein; tetrachloro-6-carboxyfluorescein (TET); hexachloro-6-carboxyfluorescein (HEX); 2,7-dimethoxy-4,5-dichloro-6-carboxyfluorescein (JOE); VIC®; NED™; tetramethylrhodamine (TMR); 5-Carboxytetramethylrhodamine (5-TAMRA); 5-HAT (Hydroxy Tryptamine); 5-Hydroxy Tryptamine (HAT); 5-ROX (carboxy-X-rhodamine); 6-Carboxyrhodamine 6G; 6-JOE; Light Cycler® red 610; Light Cycler® red 640; Light Cycler® red 670; Light Cycler® red 705; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; AutoFluorescent Proteins; Texas Red and related molecules; Thiadicarbocyanine (DiSC3); Thiazine Red R; Thiazole Orange; Thioflavin derivatives; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamine-lsoThioCyanate); True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; interchelating dyes such as YOYO-3, Sybr Green, Thiazole orange; members of the Alexa Fluor® dye series (from Molecular Probes/Invitrogen) such as Alexa Fluor 350, Alexa Fluor 405, 430, 488, 500, 514, 532, 546, 555, 568, 594, 610, 633, 635, 647, 660, 680, 700, and 750; members of the Cy Dye fluorophore series (GE Healthcare), such as Cy3, Cy3B, Cy3.5, Cy5, Cy5.5, Cy7; members of the Oyster® dye fluorophores (Denovo Biolabels) such as Oyster-500, -550, -556, 645, 650, 656; members of the DY-Labels series (Dyomics), such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL; members of the ATTO series of fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740; members of the CAL Fluor® series or Quasar® series of dyes (Biosearch Technologies) such as CAL Fluor® Gold 540, CAL Fluor® Orange 560, Quasar® 570, CAL Fluor® Red 590, CAL Fluor® Red 610, CAL Fluor® Red 635, Quasar® 570, and Quasar® 670.

Fluorescent markers may be coupled to a targeting moiety to allow specific binding or localization, for example, to a specific population of cells, of which there are many known in the art. Nonlimiting examples include antibodies, antibody fragments, antibody derivatives, aptamers, oligopeptides such as the nuclear localization sequence (NLS), small molecules that serve as specific ligands for receptors including many hormones and drugs, nucleic acid sequences (such as for FISH), nucleic acid binding proteins (including repressors and transcription factors), cytokines, ligands specific for cellular membranes, enzymes, molecules that specifically bind to enzymes (such as inhibitors), lipids, fatty acids, and members of specific binding interactions such as biotin/iminobiotin and avidin/streptavidin.

Targets for specific labeling in or on a cell may be natural or artificial and may encompass proteins, nucleic acids, lipids, carboyhydrates, small molecules, and any combinations thereof. These include intracellular and cell surface markers. Intracellular markers include any molecule, complex, or other structure within the cell. A few nonlimiting examples include genes, centromeres, telomeres, nuclear pore complexes, ribosomes, proteasomes, an internal lipid membrane, metabolites such as ATP, NADPH, and their derivatives, enzymes or enzyme complexes, protein chaperones, post-translational modifications such as phosphorylation or ubiquitinylation, microtubules, actin filaments, and many others. Cell surface markers include but are not limited to proteins such as CD4, CD8, CD45, CD2, CRTH2, CD19, CD3, CD14, CD36, CD56, CD5, CD7, CD9, CD10, CD11b, CD11c, CD13, CD15, CD16, CD20, CD21, CD22, CD23, CD24, CD25, CD33, CD34, CD37, CD38, CD41, CD42, CD57, CD122, CD52, CD60, CD61, CD71, CD79a, CD95, CD103, CD117, CD154, GPA, HLA, KOR, FMC7. In some embodiments, the targets may be specific regions within a cell, such as targeting to the interior of specific organelles or membrane-bound vesicles. In some embodiments, the target may be the result of genetic or other manipulation, such as cloning Lac binding sites into a genetic sequence for targeted binding by a labeled Lac protein.

Cells may be labeled through various means, including but not limited to surface labeling, permeabilization of the cell membrane and/or cell wall, active transport or other cellular processes, diffusion through the membrane, carrier particles such as lipid vesicles or other hydrophobic molecules, and production by the cell (such as for recombinantly fluorescent proteins).

In some embodiments, samples containing mixed populations of cells may be treated before optical detection to enrich for detection of target population(s) of cells. Some example methods for enrichment include but are not limited to centrifugation, sorting (with or without labeling), selective killing of non-target cells such as by lysis, and selective labeling to improve detection of target cells.

In embodiments, cells for use with methods or devices provided herein may be prepared or analyzed (e.g. isolated, washed, stained, imaged, etc.) as described in any of U.S. Provisional Patent App. Nos. 61/675,811, 61/676,178, 61/766,116, 61/802,194, each of which is incorporated by reference in their entirety. In some embodiments, devices or methods disclosed herein may be used with any of systems, methods, or devices as disclosed in, for example, U.S. Pat. No. 8,380,541; U.S. Pat. App. Ser. No. 61/675,811, filed Jul. 25, 2012; U.S. Patent Application 61/837,168, filed Jun. 19, 2013, entitled "METHODS AND DEVICES FOR SMALL VOLUME LIQUID CONTAINMENT"; U.S. Patent Application 61/837,151, filed Jun. 19, 2013, entitled "DEVICES, SYSTEMS, AND METHODS FOR CELL ANALYSIS IN MICROGRAVITY"; U.S. Pat. App. Ser. No. 61/676,178, filed Jul. 26, 2012; U.S. Pat. App. Ser. No. 61/766,116, filed Feb. 18, 2013; U.S. Pat. App. Ser. No. 61/802,194, filed Mar. 15, 2013; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. It should also be understood that while the invention provided herein has been described herein using a limited number of terms and phrases for purposes of expediency, the invention could also be described using other terms and phrases not provided herein which also accurately describe the invention. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. As used in the description herein and through the claims that follow, a first object described as containing "at least a portion" of a second object may contain the full amount of/the complete second object. As used in the description herein and throughout the claims that follow, the terms "comprise", "include", and "contain" and related tenses are inclusive and open-ended, and do not exclude additional, unrecited elements or method steps. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction by anyone of the patent documents or the patent disclosure, as they appear in the US Patent and Trademark Office patent file or records, but otherwise reserves all copyright rights whatsoever. The following notice shall apply: Copyright 2013-14, Theranos, Inc.

We claim:

1. A method of analyzing a biological sample, the method comprising:

dividing the biological sample into at least a first portion and a second portion, wherein both the first portion and the second portion contain multiple cells;

moving a flow sample cuvette onto the stage of a cytometry apparatus, wherein the flow sample cuvette is configured to receive and support a biological sample, wherein the flow sample cuvette contains a flow channel through which the biological sample may flow, and wherein the flow channel comprises a bottom surface, wherein the bottom surface comprises a sample plane over which the biological sample and objects therein may flow, and wherein the cytometry apparatus comprises an illumination train, wherein the illumination train comprises a light source, wherein the illumination train is configured to provide at least a first illumination output and a second illumination output, and wherein for the first illumination output the illumination train is configured to focus light of a first range of wavelengths from the light source onto a first location on the sample plane of the flow cytometry cuvette and the illumination train is configured to focus light of a second range of wavelengths from the light source on a second location on the sample plane of the flow cytometry cuvette;

using an objective and a sample coplanar light source disposed in substantially the same plane as the sample plane, wherein light from said sample coplanar light source is not in optical communication with the objective wherein the objective is optically coupled to a stage such that light from the biological sample supported by the flow sample cuvette enters the objective;

loading the first portion of the biological sample into the flow sample cuvette;

flowing the first portion of the biological sample through the flow channel of the flow sample cuvette, wherein during the flowing, light of a first range of wavelengths from the light source is focused on a first location in the flow channel and light of a second range of wavelengths from the light source is focused on a second location in the flow channel; and detecting light emitted from a cell in the first location in the flow channel and light emitted from a cell in the second location in the flow channel;

removing the flow sample cuvette from the stage of the cytometry apparatus;

moving a stationary sample cuvette to the stage of the cytometry apparatus, wherein the stationary sample cuvette is configure to receive and support a biological sample, wherein the stationary sample cuvette comprises a well for holding the biological sample in a stationary portion, wherein the well comprises side walls and a bottom surface, and wherein the bottom surface of the well comprises a sample plane on which the biological sample and objects therein may settle;

loading the second portion of the biological sample into the stationary sample cuvette; and obtaining an image of some or all of the second portion of the biological sample in the stationary sample cuvette, wherein the image includes information from at least two cells in the second portion of the biological sample.

2. The method of claim 1, wherein the cells are white blood cells.

3. The method of claim 1, wherein the first location and second location each have a diameter between about 10 and about 200 microns.

4. The method of claim 1, wherein the first location and second location each have a center, and wherein the center of the first location is separated from the center of the second location by between about 10 and about 200 microns.

5. The method of claim 1, wherein the first location and second location each have a center, and wherein the center of the first location is separated from the center of the second location by a distance of at least the average diameter size of cells in the sample.

6. The method of claim 1, wherein detecting said light comprises using a first detection train comprises at least three image sensors.

7. The method of claim 1, wherein detecting said light comprises using a second detection train comprises at least a first light detector, a second light detector, and a third light detector, wherein the detection train is configured such that the first light detector is configured to receive light of a first range of wavelengths, the second light detector is configured to receive light of a second range of wavelengths, and the third light detector is configured to receive light of a third range of wavelengths.

8. The method of claim 7, wherein the second detection train comprises a first emission filter placed before the first light detector, a second emission filter placed before second light detector, and a third emission filter placed before the third light detector.

9. The method of claim 1, wherein for the first illumination output the illumination train is further configured to focus light of a third range of wavelengths from the light source on a third location on the sample plane of the cytometry cuvette.

10. The method of claim 1, wherein the first portion of the biological sample is loaded into the stationary sample cuvette before the stationary sample cuvette is moved onto the stage of the cytometry apparatus.

11. The method of claim 1, wherein the first portion of the biological sample is loaded into the stationary sample cuvette after the stationary sample cuvette is moved onto the stage of the cytometry apparatus.

12. The method of claim 1, wherein the first location in the flow channel and the second location in the flow channel are separated from each other by at least 10 and no more than 100 microns.

13. A cytometry apparatus comprising:
  A) a stage configured to receive a cytometry cuvette having a sample plane;
  B) an objective in optical communication with an opening in the stage;
  C) a first optical pathway, wherein the first optical pathway comprises one or more image sensors;
  D) a second optical pathway, wherein the second optical pathway comprises one or more light detectors;
  E) an actuatable structure for directing the path of light, wherein the actuatable structure is configured to direct light from the objective to either the first optical pathway or the second optical pathway; and
  F) a sample coplanar light source;
wherein the objective and the sample coplanar light source disposed in substantially the same plane as the sample plane when the cuvette is received by the stage, wherein light from said sample coplanar light source is not in optical communication with the objective wherein the objective is optically coupled to said stage such that light from the biological sample supported by the flow sample cuvette enters the objective.

14. The cytometry apparatus of claim 13, wherein the apparatus is configured to receive at least two different types of cuvettes.

15. The cytometry apparatus of claim 14, wherein the apparatus is configured to receive a stationary sample cuvette and a flow sample cuvette.

16. The cytometry apparatus of claim 15, wherein the apparatus is configured to obtain data from stationary samples and moving samples.

17. The cytometry apparatus of claim 16, wherein light from stationary samples is directed to the first optical pathway, and wherein light from moving samples is directed to the second optical pathway.

18. The method of claim 1, wherein said detecting light from cells in the first location and in the second location in the flow channel comprises detecting light with at least two image sensors.

19. The method of claim 1, further comprising use of a detection train, wherein said detection train comprises at least a first light detector, a second light detector, and a third light detector, wherein the detection train is configured such that the first light detector is configured to receive light of a first range of wavelengths, the second light detector is configured to receive light of a second range of wavelengths, and the third light detector is configured to receive light of a third range of wavelengths.

20. The method of claim 19, wherein the detection train comprises a first emission filter before the first light detector, a second emission filter before second light detector, and a third emission filter before the third light detector.

* * * * *